US010792002B2

(12) United States Patent
Issani et al.

(10) Patent No.: US 10,792,002 B2
(45) Date of Patent: Oct. 6, 2020

(54) METHOD AND SYSTEM FOR DETERMINING THE POSITION OF A C-ARM OF AN X-RAY SYSTEM

(71) Applicants: Siraj Issani, Karnataka (IN); Mohd Saim Nasim Lari, Uttar Pradesh (IN); Shamlin Sunny, Kerala (IN); Vivek Warriar, Karnataka (IN)

(72) Inventors: Siraj Issani, Karnataka (IN); Mohd Saim Nasim Lari, Uttar Pradesh (IN); Shamlin Sunny, Kerala (IN); Vivek Warriar, Karnataka (IN)

(73) Assignee: Siemens Healthcare GmbH, Erlangen (DE)

(*) Notice: Subject to any disclaimer, the term of this patent is extended or adjusted under 35 U.S.C. 154(b) by 223 days.

(21) Appl. No.: 15/953,634

(22) Filed: Apr. 16, 2018

(65) Prior Publication Data

US 2018/0303454 A1 Oct. 25, 2018

(30) Foreign Application Priority Data

Apr. 20, 2017 (IN) .............................. 201731014040

(51) Int. Cl.
*A61B 6/00* (2006.01)
*A61B 6/08* (2006.01)

(52) U.S. Cl.
CPC .............. *A61B 6/465* (2013.01); *A61B 6/461* (2013.01); *A61B 6/463* (2013.01); *A61B 6/467* (2013.01);

(Continued)

(58) Field of Classification Search
CPC .... A61B 6/08; A61B 6/44; A61B 6/46; A61B 6/461; A61B 6/463; A61B 6/465;

(Continued)

(56) References Cited

U.S. PATENT DOCUMENTS 6,473,489 B2* 10/2002 Bani-Hashemi ......... A61B 6/08
378/206
2010/0111389 A1 5/2010 Strobel et al.
(Continued)

FOREIGN PATENT DOCUMENTS

DE 102014205671 A1 10/2015
DE 102014216887 B3 11/2015
(Continued)

OTHER PUBLICATIONS

European Search Report for European Patent Application No. 18167929.1-1124 dated Sep. 3, 2018.

*Primary Examiner* — Anastasia Midkiff
(74) *Attorney, Agent, or Firm* — Lempia Summerfield Katz LLC

(57) ABSTRACT

A method and system for determining the position of a C-arm of an X-ray system is disclosed. The method includes obtaining a primary X-ray image of a desired location on a patient's body, obtaining a secondary X-ray image of the desired location on the patient's body, adjusting the secondary X-ray image with respect to the primary X-ray image using one or more touch based gestures, determining the subsequent location for X-ray imaging on the patient's body, and positioning the C-arm of the X-ray system to the subsequent location for X-ray imaging on the patient's body.

19 Claims, 8 Drawing Sheets

(52) U.S. Cl.
CPC ............... *A61B 6/469* (2013.01); *A61B 6/54* (2013.01); *A61B 6/589* (2013.01); *A61B 6/08* (2013.01); *A61B 6/46* (2013.01); *A61B 6/587* (2013.01); *A61B 6/588* (2013.01)

(58) Field of Classification Search
CPC ........... A61B 6/467; A61B 6/469; A61B 6/54; A61B 6/542; A61B 6/545; A61B 6/587; A61B 6/588; A61B 6/589
See application file for complete search history.

(56) References Cited

U.S. PATENT DOCUMENTS

| | | | |
|---|---|---|---|
| 2014/0371578 A1* | 12/2014 | Auvray | A61B 6/12 600/424 |
| 2015/0297151 A1* | 10/2015 | Florent | A61B 90/10 600/424 |
| 2017/0215725 A1* | 8/2017 | Ishiai | A61B 3/0025 |
| 2017/0262602 A1 | 9/2017 | Schweizer | |
| 2017/0281110 A1* | 10/2017 | Mandelkern | A61B 6/025 |

FOREIGN PATENT DOCUMENTS

| | | |
|---|---|---|
| DE | 102014210893 A1 | 12/2015 |
| EP | 2954843 A1 | 12/2015 |
| WO | WO2015018566 A1 | 2/2015 |

\* cited by examiner

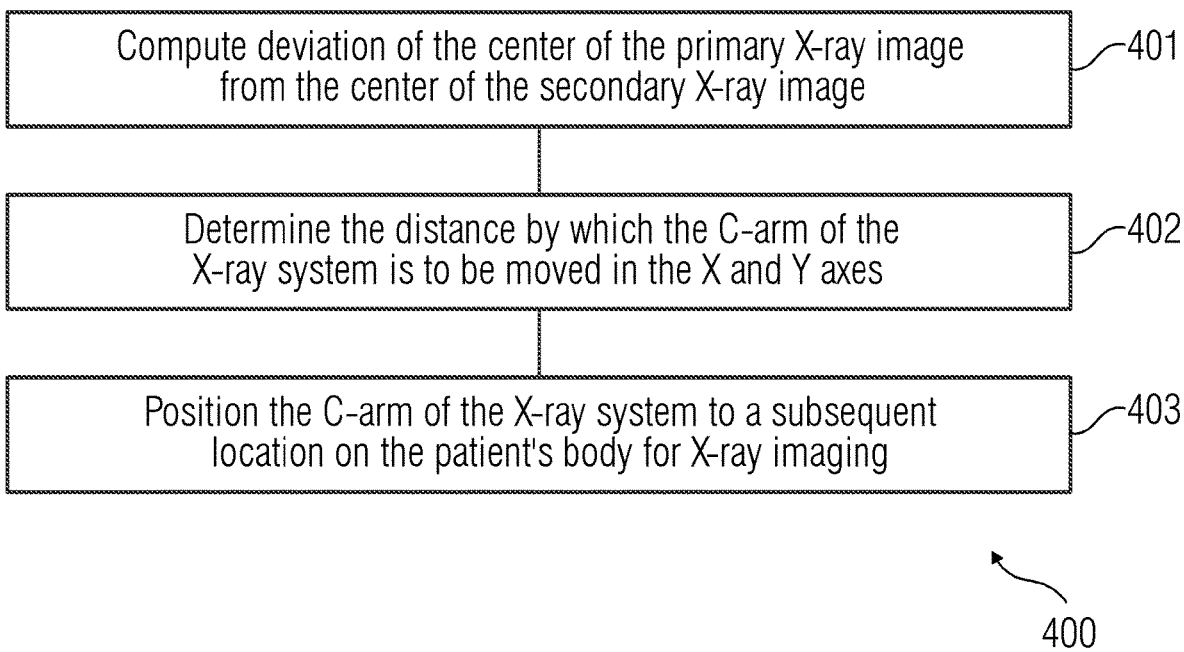

US 10,792,002 B2

METHOD AND SYSTEM FOR DETERMINING THE POSITION OF A C-ARM OF AN X-RAY SYSTEM

The application claims the benefit of Indian Patent Application No. 201731014040, filed Apr. 20, 2017, which is hereby incorporated by reference in its entirety.

FIELD OF TECHNOLOGY

The disclosure relates to the field of X-ray systems and particularly to the field of positioning of C-arms of X-ray systems.

BACKGROUND

Fluoroscopic X-ray procedures are used in interventional procedures, such as an orthopedic surgery, angiography, and percutaneous nephrolithotomy (PCNL), to determine the placement of an implant or a surgical tool inside the body of a patient. In the case of entry-level X-ray systems, the C-arm is manually positioned around the patient by the operator. The placement of the C-arm around the patient involves several constraints, such as the image field of view contains all relevant information needed to perform the surgery. For repeated procedures, a reference alignment is followed for accurate positioning of the C-arm over the patient. Furthermore, to obtain accurate field of view of the patient's body, the operator receives an X-ray image feedback after successively applying dosage to the patient. Therefore, the C-arm is positioned around the patient based on the acquired X-ray images.

In the absence of a guidance system for fluoroscopic X-ray procedures, the C-arm is positioned over the patient's body based on hit-and-trial iterations. During such hit-and-trial iterations, the patient is exposed to radiation, either continuously or intermittently, to check the position of the surgical tool in the patient's body. This adds to the total radiation dose given to the patient. Such procedures also add to the total time for the interventional procedure.

SUMMARY AND DESCRIPTION

Thus, there exists a need to determine the positioning of the C-arm of an X-ray system on a patient's body without increasing the dosage levels given to the patient.

Therefore, the object of the disclosure is to provide a method and a system for determination of the position of the C-arm of an X-ray system, which reduces the time and dosage exposures for alignment of the C-arm around the patient's body.

The scope of the present disclosure is defined solely by the appended claims and is not affected to any degree by the statements within this summary. The present embodiments may obviate one or more of the drawbacks or limitations in the related art.

A method and a system for determining the position of the C-arm of an X-ray system that reduces the time for alignment of the C-arm and reduces dosage exposure is disclosed. The object of the disclosure is met by a method to determine the position of the C-arm of an X-ray system. According to the method, a primary X-ray image of a desired location on a patient's body is obtained. The C-arm of the X-ray system is aligned around the body of the patient, and a primary X-ray image is obtained. Alternatively, the primary X-ray image may also be obtained from an image database stored in a memory of a computing device. A secondary X-ray image of the desired location on the patient's body is obtained. According to the method, the secondary X-ray image is adjusted with respect to the primary X-ray image. The adjustment of the secondary X-ray image may be performed using at least one touch based gesture. Based on the adjustment of the secondary X-ray image, a subsequent location for X-ray imaging on the patient's body is determined and the C-arm of the X-ray system is positioned according to the determined subsequent location.

According to an embodiment of the disclosure, the adjustment of the secondary X-ray image with respect to the primary X-ray image is performed by overlaying the secondary X-ray image over the primary X-ray image and changing the position of the secondary X-ray image with respect to the primary X-ray image using one or more touch based gestures. This enables an operator to accurately determine the subsequent location for X-ray imaging on the patient's body.

According to yet another embodiment of the disclosure, in determining the subsequent location for X-ray imaging, the method includes computing a deviation of the center of the primary X-ray image from the center of the secondary X-ray image and determining the distance that the C-arm of the X-ray system is to be moved in the X, Y, and Z axes.

According to an embodiment of the disclosure, the method further includes automatically positioning the C-arm of the X-ray system based on the determined subsequent location on the patient's body.

According to another embodiment of the disclosure, the secondary X-ray image is a copy of the primary X-ray image.

According to yet another embodiment of the disclosure, touch based gestures include finger or stylus based actions of swiping, tapping, scrolling, panning, rotating, and pinch to zoom.

The object of the disclosure is also achieved by a system for determining the position of the C-arm of an X-ray system. According to the disclosure, the system includes a processing unit, an image database coupled to the processing unit, and a memory coupled to the processing unit. The memory includes a positioning module that is configured to obtain a primary X-ray image of a desired location on a patient's body. The primary X-ray image may be obtained by acquiring an X-ray image of the desired location on the patient's body or from the image database coupled to the processing unit. The positioning module is also configured to obtain a secondary X-ray image of the desired location on the patient's body. The positioning module is further configured to adjust the secondary X-ray image with respect to the primary X-ray image based on the touch based gestures inputted by a user. Based on the adjustment of the secondary X-ray image with respect to the primary X-ray image, the positioning module is configured to determine the subsequent location for X-ray imaging on the patient's body. The positioning module is also configured to position the C-arm of the X-ray system to the subsequent location for X-ray imaging on the patient's body.

According to an embodiment of the disclosure, in adjusting the secondary X-ray image with respect to the primary X-ray image, the positioning module is further configured to overlay the secondary X-ray image over the primary X-ray image and configured to change the position of the secondary X-ray image with respect to the primary X-ray image based on one or more touch based gestures.

According to another embodiment of the disclosure, in determining the subsequent location for X-ray imaging, the positioning module is further configured to compute a deviation of the center of the primary X-ray image from the center of the secondary X-ray image and configured to determine the distance that the C-arm of the X-ray system is to be moved in the X, Y, and Z axes.

According to an embodiment of the disclosure, the positioning module is further configured to automatically position the C-arm of the X-ray system based on the determined subsequent location on the patient's body.

The summary is provided to introduce a selection of concepts in a simplified form that are further described below in the following description. The summary is not intended to identify features or essential features of the claimed subject matter. Furthermore, the claimed subject matter is not limited to implementations that solve any or all disadvantages noted in any part of this disclosure.

BRIEF DESCRIPTION OF THE DRAWINGS

The present disclosure is further described hereinafter with reference to illustrated embodiments depicted in the accompanying drawings, in which:

FIG. 4 is a flowchart illustrating an exemplary method for determining the subsequent location for X-ray imaging on a patient's body, according to an embodiment.

DETAILED DESCRIPTION

Figure 1:
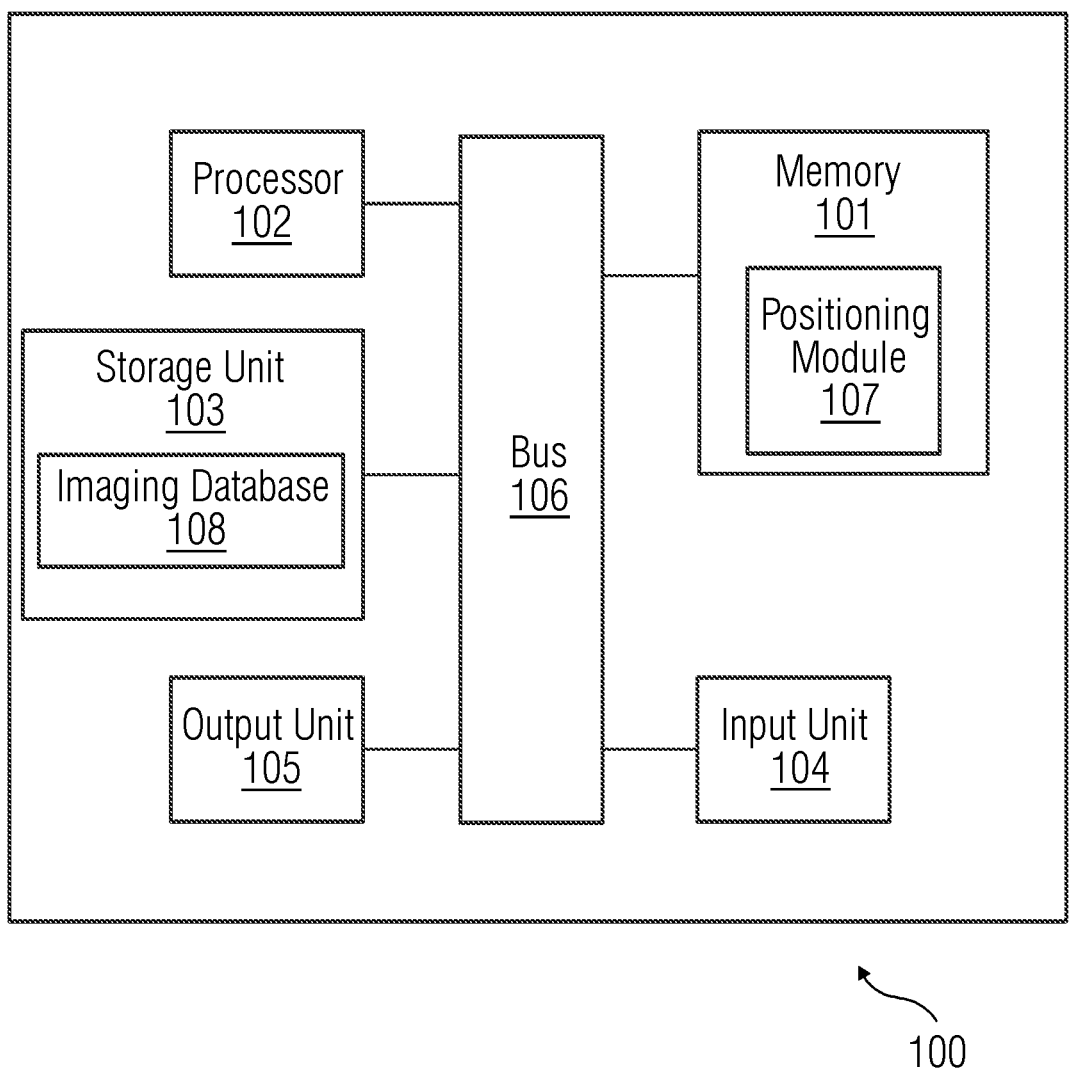
FIG. 1 illustrates a block diagram of a data processing system in which an embodiment for determining the position of a C-arm of an X-ray system may be implemented.

Hereinafter, embodiments for carrying out the present disclosure are described in detail. The various embodiments are described with reference to the drawings, wherein like reference numerals are used to refer to like elements throughout. In the following description, for purpose of explanation, numerous specific details are set forth in order to provide a thorough understanding of one or more embodiments. It may be evident that such embodiments may be practiced without these specific details. In other instances, well known materials or methods have not been described in detail to avoid unnecessarily obscuring embodiments of the present disclosure. While the disclosure is capable of various modifications and alternative forms, specific embodiments thereof are depicted by way of example in the drawings and will herein be described in detail. It should be understood, however, that there is no intent to limit the disclosure to the forms disclosed, but on the contrary, the disclosure is to cover all modifications, equivalents, and alternatives falling within the spirit and scope of the present disclosure.

FIG. 1 illustrates a data processing system 100 in which an embodiment of a method may be implemented as a system to determine the position of a C-arm of an X-ray system, where the system is configured to perform the processes as described herein. In FIG. 1, the data processing system 100 includes a memory 101, a processor 102, a storage unit 103, an input unit 104, an output unit 105, and a bus 106.

The processor 102, as used herein, refers to any type of computational circuit, such as, but not limited to, a microprocessor, microcontroller, complex instruction set computing microprocessor, reduced instruction set computing microprocessor, very long instruction word microprocessor, explicitly parallel instruction computing microprocessor, graphics processor, digital signal processor, or any other type of processing circuit. The processor 102 may also include embedded controllers, such as generic or programmable logic devices or arrays, application specific integrated circuits, single-chip computers, and the like.

The memory 101 may be volatile memory and/or non-volatile memory. The memory 101 may be coupled for communication with the processor 102. The processor 102 may execute instructions and/or code stored in the memory 101. A variety of computer-readable storage media may be stored in and accessed from the memory 101. The memory 101 may include any suitable elements for storing data and machine-readable instructions, such as read only memory, random access memory, erasable programmable read only memory, electrically erasable programmable read only memory, a hard drive, a removable media drive for handling compact disks, digital video disks, diskettes, magnetic tape cartridges, memory cards, and the like. In the present embodiment, the memory 101 includes a positioning module 107 stored in the form of machine-readable instructions on any of the above-mentioned storage media and may be in communication with and executed by processor 102. When executed by the processor 102, the positioning module 107 causes the processor 102 to determine the position of the C-arm of an X-ray system around a patient's body. Method acts executed by the processor 102 to achieve the above-mentioned functionality are elaborated upon in detail in FIGS. 2, 3, and 4.

The storage unit 103 may be a non-transitory storage medium, which stores an imaging database 108. The imaging database 108 is a repository of X-ray images related to one or more patients that is maintained by a healthcare service provider. The input unit 104 may include an input device such as keypad, a touch-sensitive display, a camera (such as a camera receiving gesture-based inputs), etc. that are capable of receiving input signals, such as positioning information of the X-ray images. The output unit 105 output the results of operations performed by the positioning module 107. For example, the positioning module 107 provides data pertaining to a location of subsequent X-ray imaging on a patient's body using the output unit 105. The output unit 105, via the graphical user interface (GUI), displays information such as user interface elements, e.g. text fields, buttons, windows, etc., for allowing a user to provide his/her inputs, such as the protection units for each of the sections of the power network. The output unit 105 includes, for example, a liquid crystal display, a plasma display, an organic light emitting diode (OLED) based on the display, etc. The bus 106 acts as an interconnect between the processor 102, the memory 101, the storage unit 103, the output unit 105, and the input unit 104.

Those of ordinary skill in the art will appreciate that the hardware depicted in FIG. 1 may vary for particular implementations. For example, other peripheral devices, such as an optical disk drive and the like, Local Area Network (LAN)/Wide Area Network (WAN)/Wireless (e.g., Wi-Fi) adapter, graphics adapter, disk controller, input/output (I/O) adapter, also may be used in addition or in place of the hardware depicted. The depicted example is provided for the purpose of explanation only and is not meant to imply architectural limitations with respect to the present disclosure.

A data processing system in accordance with an embodiment of the present disclosure includes an operating system employing a graphical user interface. The operating system permits multiple display windows to be presented in the graphical user interface simultaneously with each display window providing an interface to a different application or to a different instance of the same application. A cursor in the graphical user interface may be manipulated by a user through the pointing device. The position of the cursor may be changed and/or an event, such as clicking a mouse button or touch based gestures, may be generated to actuate a desired response.

One of various commercial operating systems, such as a version of Microsoft Windows™, a product of Microsoft Corporation located in Redmond, Wash. may be employed if suitably modified. The operating system is modified or created in accordance with the present disclosure as described.

Disclosed embodiments provide systems and methods for determining the position of a C-arm of an X-ray system. In particular, the systems and methods may determine the subsequent location for X-ray imaging on a patient's body.

Figure 2:
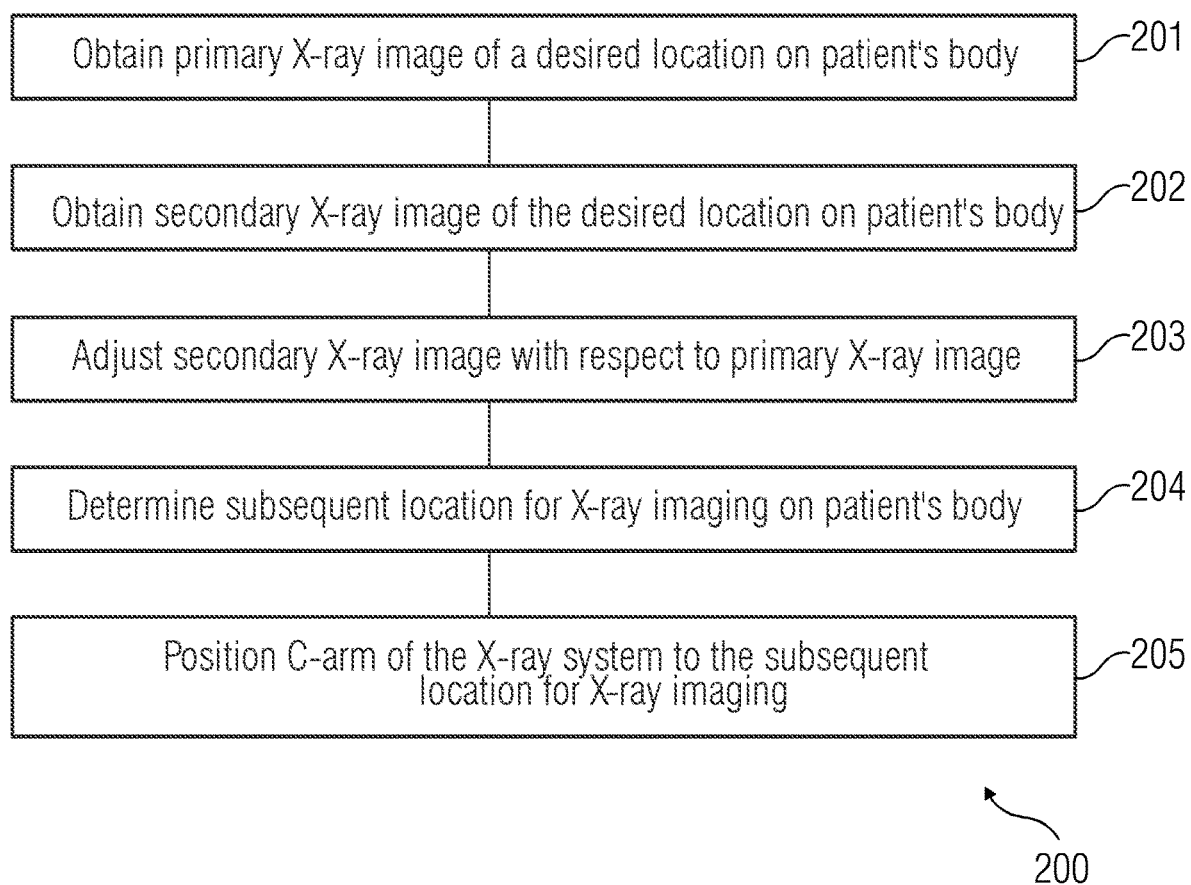
FIG. 2 is a flowchart illustrating an exemplary method for determining the position of a C-arm of an X-ray system, according an embodiment.
Figure 3:
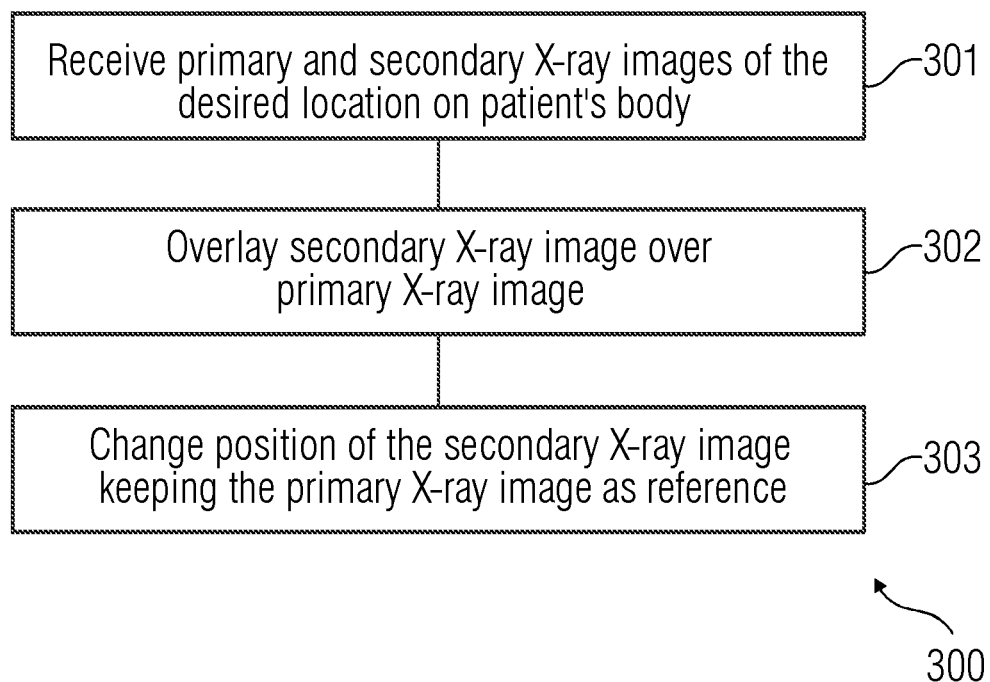
FIG. 3 is a flowchart illustrating an exemplary method for adjusting the X-ray images, according to an embodiment.
Figure 5A:
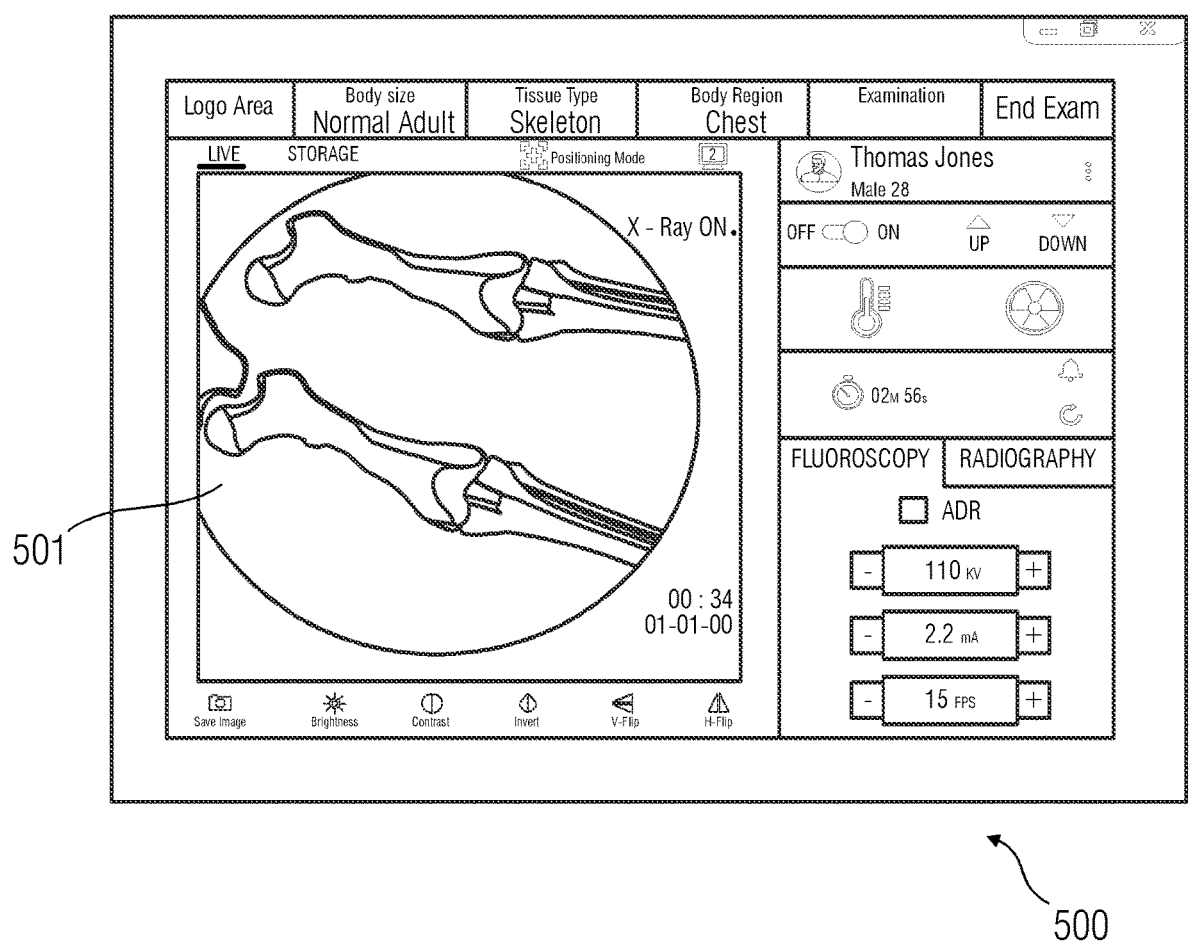
FIG. 5A illustrates a graphical user interface for determining the position of a C-arm of an X-ray system, according to an embodiment.
Figure 5B:
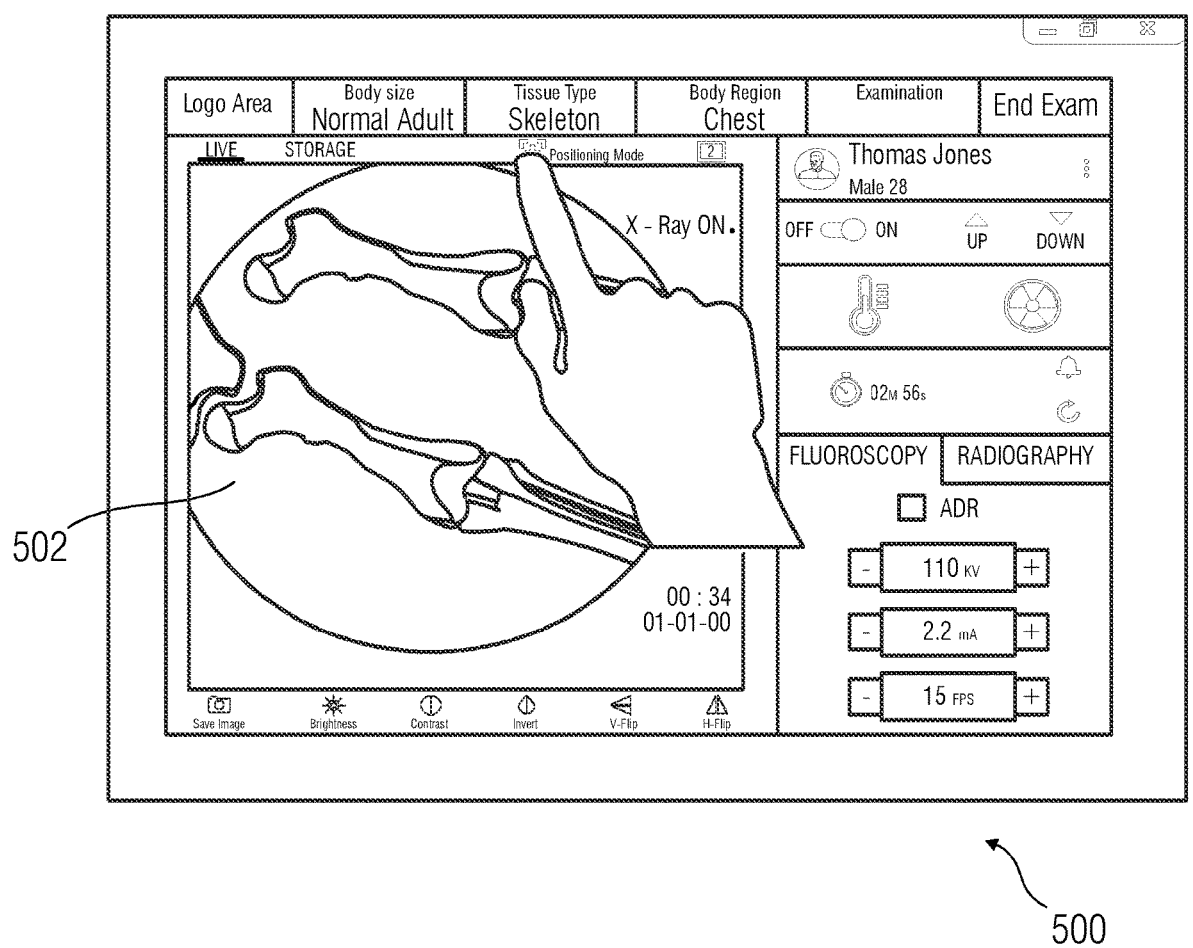
FIG. 5B illustrates a graphical user interface displaying an obtaining of a secondary X-ray image, according to an embodiment.

FIG. 2 illustrates a flowchart of an embodiment of an exemplary method 200 for determining the position of a C-arm of an X-ray system. At act 201, a primary X-ray image of a desired location on a patient's body is obtained. The primary X-ray image may be obtained by acquiring an X-ray image using the X-ray system. Alternatively, the primary X-ray image may also be obtained from an imaging database 108 stored in the storage unit 103 of the data processing system 100. The obtained primary X-ray image may be displayed on a handheld device, which is connected to the X-ray system through a communication interface. During a surgical procedure, in order to determine the location of the surgical tool, (such as catheter, inside the patient's body), the subsequent location of the X-ray imaging should be accurately determined. FIGS. 5A and 5B illustrate a graphical user interface 500 for determination of the position of the C-arm of an X-ray system displayed on the handheld device. The graphical user interface 500 depicts a field of view 501 depicting the primary X-ray image. The graphical user interface 500 also depicts features of the X-ray imaging system that are required for acquisition of X-ray images by the X-ray system.

Figure 5C:
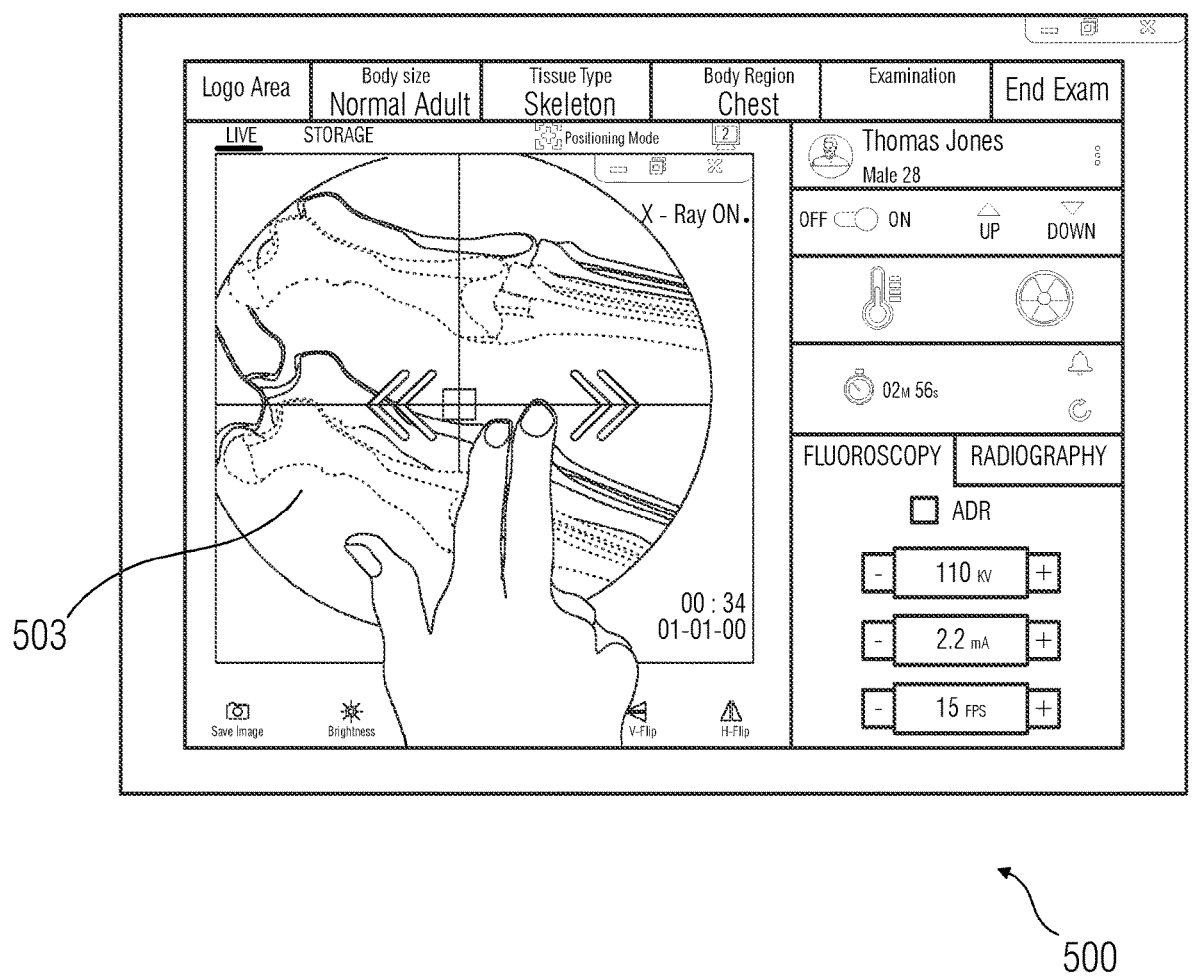
FIG. 5C illustrates a graphical user interface displaying an overlay of X-ray images to determine the subsequent location for X-ray imaging on the patient's body, according to an embodiment.

At act 202, a secondary X-ray image of the desired location on the patient's body is obtained. The secondary X-ray image is a copy of the primary X-ray image. The graphical user interface 500 also includes an option to create a reference image-overlay on top of the primary X-ray image, which is depicted as 'Positioning Mode' in FIG. 5B. The graphical user interface 500, with a field of view 502, enables activation of the 'Positioning Mode' by an operator using the touch based gestures. On activation of the 'Positioning Mode', a copy of the primary X-ray image is obtained and a reference image-overlay over the primary X-ray image is created. FIG. 5C illustrates a graphical user interface 500 in which the reference image-overlay of the primary X-ray image and the secondary X-ray image is depicted in the field of view 503.

At act 203, on creation of the image-overlay, the secondary X-ray image is adjusted with respect to the primary X-ray image using touch based gestures. The touch based gestures may include, but are not limited to, finger or stylus based actions of swiping, tapping, scrolling, panning, rotating, and pinch to zoom. The graphical user interface 500 in FIG. 5C also illustrates the adjustment of the secondary X-ray image with respect to the primary X-ray image using touch based gestures. The aspect of adjusting the secondary X-ray image with respect to the primary X-ray image is explained further in FIG. 3, wherein, on receiving the primary and secondary X-ray images of the desired location at act 301, the secondary X-ray image is overlaid on the primary X-ray image at act 302. At act 303, the position of the secondary X-ray image is changed, thereby keeping the primary X-ray image as a reference. When repositioned, the part of the secondary X-ray image that is not overlapping with the primary X-ray image changes colors, which indicates to the user that there is a difference in the relative position or orientation of the two X-ray images. When the primary and the secondary X-ray images perfectly overlap, the color of the X-ray images again turns to black.

Based on the position to which the secondary X-ray image is moved at act 204, the subsequent location for X-ray imaging on the patient's body is determined. At act 205, the C-arm of the X-ray system is positioned to the subsequent location for X-ray imaging. On positioning the C-arm to the subsequent location on the patient's body, the subsequent X-ray image obtained is the new primary X-ray image for further processing.

FIG. 4 illustrates a flowchart of an embodiment of a method 400 for determining the subsequent location for X-ray imaging on a patient's body. At act 401, on adjusting the secondary X-ray image with respect to the primary X-ray image, the deviation of the center of the primary X-ray image from the center of the secondary X-ray image is computed. When the primary X-ray image is acquired from the X-ray system, the physical dimensions of the collimator tube of the X-ray system are mapped with the pixel dimensions of the handheld device. As the diameter and the center of the collimator tube are known entities, when an X-ray image is generated on the handheld device, the pixel dimension of the collimator tube and the center of the X-ray image are determined. The center of the X-ray image is coincident with the center of the collimator tube. Based on the resolution of the handheld device, the conversion factor from physical dimensions of the collimator tube to pixels is calculated. When the secondary X-ray image is adjusted with respect to the primary X-ray image, the deviation of the center of the primary X-ray image from the center of the secondary X-ray image is calculated. The shift in the position of the X-ray image may be termed as 'image transformation'.

At act 402, the distance by which the C-arm of the X-ray system is to be moved in the X, Y, and Z axes is determined based on the deviation of the center of the primary X-ray image from the center of the secondary X-ray image. At act 403, the C-arm of the X-ray system is positioned to a subsequent location for X-ray imaging on the patient's body. The positioning module 107 may also be configured to automatically position the C-arm of the X-ray system to the subsequent location of X-ray imaging based on these calculated parameters. The movement of the C-arm is geometrically constrained due to the pivot effect on the X-rays.

In the limiting conditions, the movement of the image is equal and opposite to the movement of the C-arm if an object point on the location of X-ray imaging on the patient's body is very close to the imaging plane. Hence, the translation or rotation in the image transformation is same as that of the C-arm itself. However, as the object point on the location of X-ray imaging on the patient's body moves away from the detector and closer to the X-ray source, the image transformation is scaled by a factor, e.g., the magnification factor (M). If an object, whose X-ray image is to be obtained, is situated at a distance 'd' from the X-ray source, the X-ray image formed is magnified by:

$$M = \frac{D}{d}$$

where D is the distance between the detector and the X-ray source.

If the object is close to the detector, the magnification factor is 1 because the movement of the C-arm makes equal and opposite movement of the X-ray image.

The user specified gestures are converted into (a) Translation: P ($X_{image}$, $Y_{image}$) in pixels; (b) Rotation: R in degrees; and (c) Zoom scale: S in percentage.

A 2D scaled affine transformation is computed as T=affine (P, R, S).

The size of the pixels (pixel-pitch) in millimeters ($\beta$), the system magnification factor (M), and the fixed distance between the X-ray source and detector ($D_{SAD}$) are determined and an affine transformation of the inverse transformation is built:

$$[X_{C-arm}, Y_{C-arm}] = T^{-1} * P * \beta$$

The co-ordinates on the Z-axis for the movement of the C-arm are determined by:

$$\frac{D_{SAD}}{M}\left(1 - \frac{1}{S}\right)$$

Figure 5D:
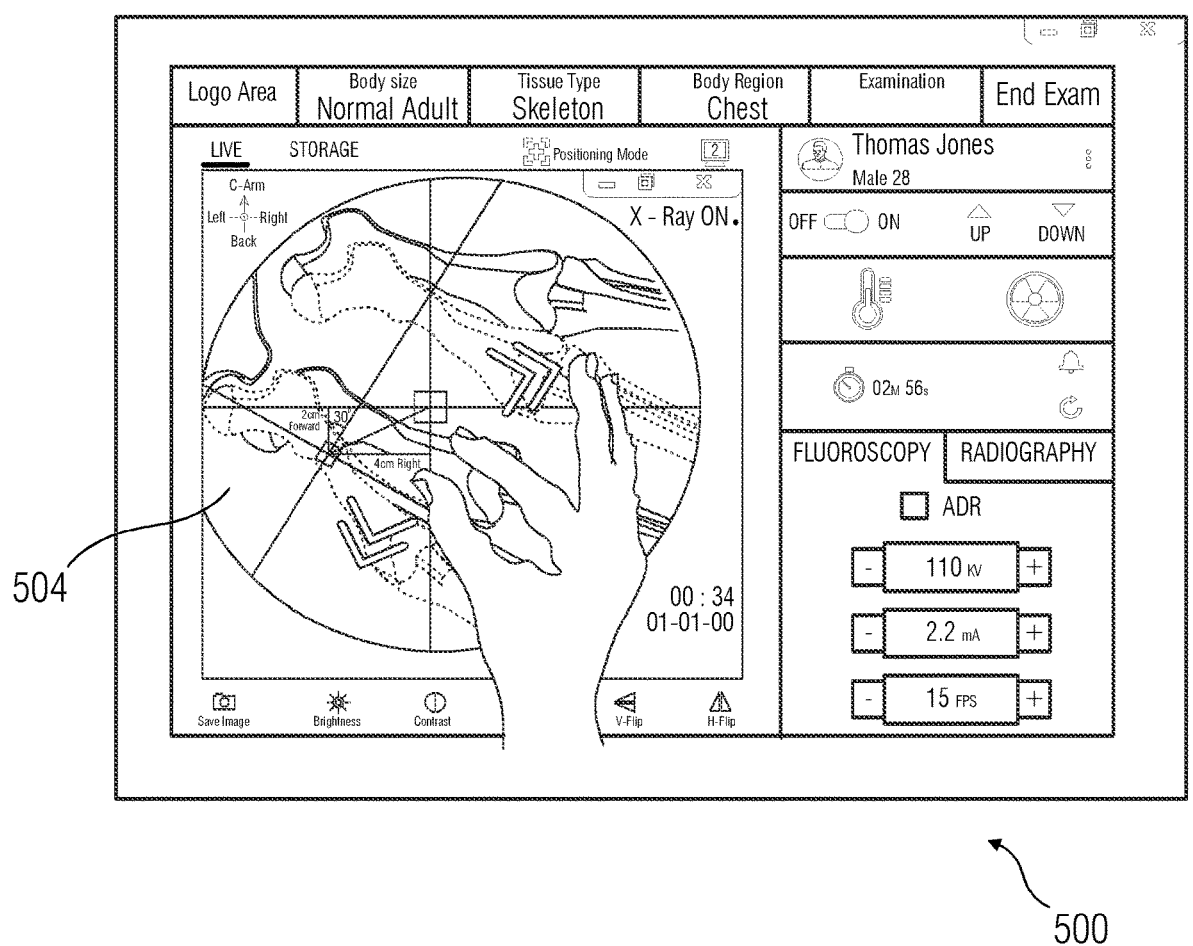
FIG. 5D illustrates a graphical user interface displaying an adjustment of a secondary X-ray image with respect to the primary X-ray image to determine the subsequent location for X-ray imaging on the patient's body, according to an embodiment.

FIG. 5D illustrates a graphical user interface 500 displaying adjustment of the secondary X-ray image with respect to the primary X-ray image to determine the subsequent location for X-ray imaging on the patient's body. The field of view 504 depicts adjustment of the secondary X-ray image with respect to the primary X-ray image. Based on the adjustment, the deviation of the center of the secondary X-ray image from the center of the primary X-ray image is calculated and displayed to the user on the screen of the handheld device. The positioning module determines the position of the C-arm of the X-ray system for subsequent imaging of the patient's body based on the calculated deviation.

The disclosed method and system for determining the position of a C-arm of an X-ray system is a user-interface only solution. Therefore, no additional hardware or system configuration over the existing X-ray system is required. The computations for the overlay of images and information are performed on the handheld device and not on the C-arm hardware. Therefore, the effort of the user to manipulate the X-ray system is reduced. Furthermore, with X-ray image overlay, the user gets a more amenable feedback, therefore improving the accuracy of the subsequent X-ray imaging in interventional procedures. This also enables reduction of X-ray dosage exposure to the patient.

It is to be understood that the elements and features recited in the appended claims may be combined in different ways to produce new claims that likewise fall within the scope of the present disclosure. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

While the present disclosure has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A method for determining a position of a C-arm of an X-ray system, the method comprising:
    obtaining a primary X-ray image of a desired location on a patient's body;
    obtaining a secondary X-ray image of the desired location on the patient's body;
    overlaying the secondary X-ray image over the primary X-ray image;
    displaying the primary X-ray image and the overlaid secondary X-ray image on a touch-sensitive display;
    adjusting a position of the secondary X-ray image with respect to the primary X-ray image based on at least one touch-based gesture on the touch-sensitive display to provide an adjusted secondary X-ray image;
    determining a subsequent location for X-ray imaging on the patient's body using the adjusted secondary X-ray image; and
    positioning the C-arm of the X-ray system to the subsequent location for X-ray imaging on the patient's body.

2. The method of claim 1, wherein the determining comprises:
    computing a deviation of a center of the primary X-ray image from a center of the adjusted secondary X-ray image; and
    determining a distance that the C-arm of the X-ray system is to be moved along one or more of an X, Y, or Z axis using the computed deviation.

3. The method of claim 1, further comprising:
    automatically positioning the C-arm of the X-ray system based on the determined subsequent location on the patient's body.

4. The method of claim 1, wherein the secondary X-ray image is a copy of the primary X-ray image.

5. The method of claim 1, further comprising:
    obtaining an X-ray image at the subsequent location on the patient's body.

6. The method of claim 1, wherein the at least one touch-based gesture comprises a finger or a stylus based action of swiping, tapping, scrolling, panning, rotating, and pinch to zoom on the touch-sensitive display.

7. A system for determining a position of a C-arm of an X-ray system, the system comprising:
    a touch-sensitive display;
    a processing unit;
    an image database coupled to the processing unit;
    a memory coupled to the processing unit, the memory comprising a positioning module configured to:

obtain a primary X-ray image of a desired location on a patient's body;

obtain a secondary X-ray image of the desired location on the patient's body;

overlay the secondary X-ray image over the primary X-ray image;

displaying the primary X-ray image and the overlaid secondary X-ray image on the touch-sensitive display;

adjust the secondary X-ray image with respect to the primary X-ray image based on at least one touch-based gesture on the touch-sensitive display to provide an adjusted secondary X-ray image;

determine a subsequent location for X-ray imaging on the patient's body using the adjusted secondary X-ray image; and position the C-arm of the X-ray system to the subsequent location for X-ray imaging on the patient's body.

8. The system of claim 7, wherein the positioning module is further configured to:

compute a deviation of a center of the primary X-ray image from a center of the adjusted secondary X-ray image; and determine a distance that the C-arm of the X-ray system is to be moved in X, Y and Z axes.

9. The system of claim 7, wherein the positioning module is further configured to automatically position the C-arm of the X-ray system based on the determined subsequent location on the patient's body.

10. The method of claim 2, further comprising:
automatically positioning the C-arm of the X-ray system based on the determined subsequent location on the patient's body.

11. The method of claim 10, wherein the secondary X-ray image is a copy of the primary X-ray image.

12. The method of claim 11, further comprising:
obtaining an X-ray image at the subsequent location on the patient's body.

13. The method of claim 12, wherein the at least one touch-based gesture comprises a finger or a stylus based action of swiping, tapping, scrolling, panning, rotating, and pinch to zoom on the touch-sensitive display.

14. The method of claim 2, wherein the secondary X-ray image is a copy of the primary X-ray image.

15. The method of claim 14, further comprising:
obtaining an X-ray image at the subsequent location on the patient's body.

16. The method of claim 15, wherein the at least one touch-based gesture comprises a finger or a stylus based action of swiping, tapping, scrolling, panning, rotating, and pinch to zoom on the touch-sensitive display.

17. The method of claim 2, further comprising:
obtaining an X-ray image at the subsequent location on the patient's body.

18. The method of claim 17, wherein the at least one touch-based gesture comprises a finger or a stylus based action of swiping, tapping, scrolling, panning, rotating, and pinch to zoom on the touch-sensitive display.

19. The method of claim 2, wherein the at least one touch-based gesture comprises a finger or a stylus based action of swiping, tapping, scrolling, panning, rotating, and pinch to zoom on the touch-sensitive display.

\* \* \* \* \*